(12) United States Patent
Teles et al.

(10) Patent No.: US 8,404,901 B2
(45) Date of Patent: Mar. 26, 2013

(54) PROCESS FOR PURIFYING DINITROGEN MONOXIDE

(75) Inventors: Joaquim Henrique Teles, Otterstadt (DE); Dieter Baumann, Speyer (DE); Beatrice Rößler-Feigel, Weisenheim am Sand (DE)

(73) Assignee: BASF SE, Ludwigshafen (DE)

( * ) Notice: Subject to any disclaimer, the term of this patent is extended or adjusted under 35 U.S.C. 154(b) by 239 days.

(21) Appl. No.: 12/936,331

(22) PCT Filed: Mar. 13, 2009

(86) PCT No.: PCT/EP2009/052992
§ 371 (c)(1),
(2), (4) Date: Oct. 4, 2010

(87) PCT Pub. No.: WO2009/121707
PCT Pub. Date: Oct. 8, 2009

(65) Prior Publication Data
US 2011/0023538 A1 Feb. 3, 2011

(30) Foreign Application Priority Data
Apr. 2, 2008 (EP) .................... 08153953

(51) Int. Cl.
*C07C 45/00* (2006.01)
*C07C 43/00* (2006.01)
*F25J 3/08* (2006.01)

(52) U.S. Cl. .............. 568/408; 568/952; 62/617

(58) Field of Classification Search ............... 568/408, 568/952
See application file for complete search history.

(56) References Cited

U.S. PATENT DOCUMENTS

| | | | |
|---|---|---|---|
| 2,636,898 A | 4/1953 | Buckley | |
| 3,656,899 A | 4/1972 | Baechle et al. | |
| 4,177,645 A | 12/1979 | Schwarz | |
| 5,401,884 A | 3/1995 | Diercks et al. | |
| 5,849,257 A | 12/1998 | Fujiwara et al. | |
| 6,080,226 A | 6/2000 | Dolan et al. | |
| 6,370,911 B1 | 4/2002 | Zhou et al. | |
| 6,387,161 B1 | 5/2002 | Zhou et al. | |
| 6,505,482 B2 | 1/2003 | Zhou et al. | |
| 7,105,704 B2 | 9/2006 | Panov et al. | |
| 7,282,612 B2 | 10/2007 | Panov et al. | |
| 7,449,606 B2 | 11/2008 | Teles et al. | |
| 7,692,045 B2 | 4/2010 | Teles et al. | |
| 2008/0274032 A1 | 11/2008 | Teles et al. | |
| 2008/0275276 A1 | 11/2008 | Teles et al. | |
| 2009/0227815 A1 | 9/2009 | Teles et al. | |
| 2010/0018389 A1 | 1/2010 | Baumann et al. | |

FOREIGN PATENT DOCUMENTS

| | | |
|---|---|---|
| DE | 2040219 A1 | 3/1971 |
| DE | 2732267 A1 | 1/1979 |
| DE | 19605211 A1 | 8/1997 |
| DE | 102005055588 A1 | 5/2007 |
| EP | 0624565 A1 | 11/1994 |
| EP | 1076217 A2 | 2/2001 |
| EP | 06125807.5 | 12/2006 |
| GB | 649680 A | 1/1951 |
| GB | 1327401 A | 8/1973 |
| WO | WO-98/25698 A1 | 6/1998 |
| WO | WO-00/01654 A1 | 1/2000 |
| WO | WO-00/73202 A1 | 12/2000 |
| WO | WO-03/078370 A1 | 9/2003 |
| WO | WO-03/078371 A1 | 9/2003 |
| WO | WO-03/078372 A1 | 9/2003 |
| WO | WO-03/078374 A1 | 9/2003 |
| WO | WO-03/078375 A1 | 9/2003 |
| WO | WO-04/000777 A1 | 12/2003 |
| WO | WO-2004/096745 A1 | 11/2004 |
| WO | WO-2005/030689 A2 | 4/2005 |
| WO | WO-2005/030690 A2 | 4/2005 |
| WO | WO-2006/032502 A1 | 3/2006 |

*Primary Examiner* — Sikarl Witherspoon
(74) *Attorney, Agent, or Firm* — Novak Druce Connolly Bove + Quigg LLP

(57) ABSTRACT

The present invention relates to a process for purifying a gas mixture comprising dinitrogen monoxide, at least comprising the at least partial condensation of a gas mixture G-I comprising dinitrogen monoxide to obtain a liquid composition C-1 comprising dinitrogen monoxide, and the contacting of the composition C-1 with a gas mixture M-1 to obtain a composition C-2 and a gas mixture M-2.

8 Claims, No Drawings

PROCESS FOR PURIFYING DINITROGEN MONOXIDE

CROSS-REFERENCE TO RELATED APPLICATIONS

This application is a national stage application (under 35 U.S.C. §371) of PCT/EP2009/052992, filed Mar. 13, 2009, which claims benefit of European application 08153953.8, filed Apr. 2, 2008.

BACKGROUND OF THE INVENTION

The present invention relates to a process for purifying a gas mixture comprising dinitrogen monoxide, at least comprising the at least partial condensation of a gas mixture G-I comprising dinitrogen monoxide to obtain a liquid composition C-1 comprising dinitrogen monoxide, and the contacting of the composition C-1 with a gas mixture M-1 to obtain a composition C-2 and a gas mixture M-2.

The prior art discloses various preparation processes and purification processes for dinitrogen monoxide. It is likewise known that dinitrogen monoxide can be used, for example, as an oxidizing agent for olefins.

For instance, WO 98/25698 discloses a process for preparing dinitrogen monoxide by catalytic partial oxidation of $NH_3$ with oxygen. According to WO 98/25698, a catalyst composed of manganese oxide, bismuth oxide and aluminum oxide is used, which leads to dinitrogen monoxide with high selectivity. A similar catalyst system is also described in detail in a scientific study (Noskov et al., Chem. Eng. J. 91 (2003) 235-242). U.S. Pat. No. 5,849,257 likewise discloses a process for preparing dinitrogen monoxide by oxidation of ammonia. The oxidation takes place in the presence of a copper-manganese oxide catalyst.

In the process disclosed in WO 00/01654, dinitrogen monoxide is prepared by reducing a gas stream comprising $NO_x$ and ammonia.

The oxidation of an olefinic compound to an aldehyde or a ketone by means of dinitrogen monoxide is described, for example, in GB 649,680 or the equivalent U.S. Pat. No. 2,636,898. Both documents quite generally disclose that the oxidation can in principle be effected in the presence of a suitable oxidation catalyst.

The more recent scientific articles of G. I. Panov et al., "Non-Catalytic Liquid Phase Oxidation of Alkenes with Nitrous Oxide. 1. Oxidation of Cyclohexene to Cyclohexanone", React. Kinet. Catal. Lett. Vol. 76, No. 2 (2002) p. 401-405, and K. A. Dubkov et al., "Non-Catalytic Liquid Phase Oxidation of Alkenes with Nitrous Oxide. 2. Oxidation of Cyclopentene to Cyclopentanone", React. Kinet. Catal. Lett. Vol. 77, No. 1 (2002) p. 197-205 likewise describe oxidations of olefinic compounds with dinitrogen monoxide. A scientific article "Liquid Phase Oxidation of Alkenes with Nitrous Oxide to Carbonyl Compounds" by E. V. Starokon et al. in Adv. Synth. Catal. 2004, 346, 268-274 also includes a mechanistic study of the oxidation of alkenes with dinitrogen monoxide in the liquid phase.

The synthesis of carbonyl compounds from alkenes with dinitrogen monoxide is also described in various international patent applications. For instance, WO 03/078370 discloses a process for preparing carbonyl compounds from aliphatic alkenes with dinitrogen monoxide. The reaction is carried out at temperatures in the range from 20 to 350° C. and pressures of from 0.01 to 100 atm. WO 03/078374 discloses a corresponding process for preparing cyclohexanone. According to WO 03/078372, cyclic ketones having from 4 to 5 carbon atoms are prepared. According to WO 03/078375, cyclic ketones are prepared under these process conditions from cyclic alkenes having from 7 to 20 carbon atoms. WO 03/078371 discloses a process for preparing substituted ketones from substituted alkenes. WO 04/000777 discloses a process for reacting di- and polyalkenes with dinitrogen monoxide to give the corresponding carbonyl compounds. The purification of dinitrogen monoxide is not mentioned in these documents.

It is likewise known that offgas streams comprising dinitrogen monoxide can be used for further reactions. Dinitrogen monoxide is obtained as an undesired by-product in various chemical processes, especially in oxidations with nitric acid and there very particularly in the oxidation of cyclohexanone and/or cyclohexanol to adipic acid. Other examples of processes in which dinitrogen monoxide is obtained as an undesired by-product are the oxidation of cyclododecanone and/or cyclododecanol with nitric acid to give dodecanedicarboxylic acid, the oxidation of acetaldehyde with nitric acid to glyoxal and the partial oxidation of $NH_3$ to NO.

For instance, WO 2005/030690, WO 2005/030689 and WO 2004/096745 disclose processes for oxidizing olefins with dinitrogen monoxide, specifically the oxidation of cyclododecatriene, of cyclododecene and of cyclopentene. All three applications disclose that, in addition to other dinitrogen monoxide sources, it is also possible to use offgas streams which can be purified, for example, by distillative methods before they are used as oxidizing agents.

Both in the preparation of dinitrogen monoxide and in the use of offgas streams, $N_2O$ is obtained initially as a dilute gaseous mixture with other components. These components can be divided into those which have a disruptive effect for specific applications and those which behave inertly. For use as an oxidizing agent, gases having a disruptive effect include $NO_x$ or, for example, oxygen ($O_2$). The term "$NO_x$", as understood in the context of the present invention, refers to all compounds $N_aO_b$ where a is 1 or 2 and b is a number from 1 to 6, except $N_2O$. Instead of the term "$NO_x$", the term "nitrogen oxides" is also used in the context of the present invention. Disruptive secondary components also include $NH_3$ and organic acids.

For specific applications, it is necessary to purify the dinitrogen monoxide used before the reaction. For example, for the use of dinitrogen monoxide as an oxidizing agent, it is necessary to remove disruptive secondary components such as oxygen or nitrogen oxides $NO_x$.

Processes for removing $NO_x$ are known in principle from the prior art. A review is given, for example, by M. Thiemann et. al in Ullmann's Encyclopedia, 6th Edition, 2000, Electronic Edition, Chapter "Nitric Acid, Nitrous Acid, and Nitrogen Oxides", Section 1.4.2.3.

The application WO 00/73202 describes a method as to how $NO_x$ and $O_2$ can be removed from an $N_2O$-containing gas stream. The $NO_x$ is removed by catalytic reduction with $NH_3$ and oxygen by catalytic reduction with hydrogen or other reducing agents. However, this method has the disadvantage that the product is contaminated with $NH_3$. A high depletion of oxygen is possible only when a loss of $N_2O$ is accepted (of, for example, from 3 to 5% of the amount originally present).

For specific applications, it may be necessary also to remove the inert compounds, since they can slow the desired reaction with $N_2O$ by dilution. The term "inert gas", as used in the context of the present invention, refers to a gas which behaves inertly with regard to the reaction of $N_2O$ with an olefin, i.e. reacts under the conditions of the reaction of olefins with $N_2O$ neither with the olefins nor with $N_2O$. Inert gases include, for example, nitrogen, carbon dioxide, argon, methane, ethane and propane. However, the inert gases can lower the space-time yield, so that a depletion can likewise be advantageous. However, it may likewise be advantageous to obtain a gas mixture which still comprises inert gases, such as carbon dioxide, and then can be used directly in a further reaction.

DE 27 32 267 A1 discloses, for example, a process for purifying dinitrogen monoxide, wherein nitrogen oxide, nitrogen dioxide, carbon dioxide and water are initially removed and the gas mixture is subsequently liquefied by compression to from 40 to 300 bar and cooling to from 0 to −88° C. From this liquefied gas mixture, dinitrogen monoxide is then removed. Although this method achieves a purification and concentration of the $N_2O$, it is economically unattractive owing to the required high pressure (60 bar), the low temperatures (−85° C.) and the associated high capital costs.

U.S. Pat. No. 4,177,645 discloses a process for removing dinitrogen monoxide from offgas streams which likewise comprises a prepurification and a low temperature distillation. The application EP 1 076 217 A1 likewise describes a method for removing low-boiling impurities from $N_2O$ by low temperature distillation.

U.S. Pat. Nos. 6,505,482, 6,370,911 and 6,387,161 also disclose processes for purifying dinitrogen monoxide, in which a low temperature distillation is in each case carried out in a special plant.

However, as a result of the high pressures and low temperatures, a low temperature distillation entails high apparatus demands, which make the purification of the dinitrogen monoxide with such a process inconvenient and costly. Particularly troublesome in this context is the fact that the melting point of $N_2O$ at standard pressure is only 3 K below the boiling point. It is therefore necessary to employ high pressures.

DE 20 40 219 discloses a preparation process for dinitrogen monoxide, wherein the dinitrogen monoxide obtained is concentrated and purified after the synthesis. According to DE 20 40 219, dinitrogen monoxide is prepared initially by oxidizing ammonia. The dinitrogen monoxide prepared is purified by separating the oxidized gases and concentrating by absorption under high pressure, which is followed by a desorption under reduced pressure. Secondary components are removed, for example, by treatment with an alkali solution in a wash tower. According to DE 20 40 219, water is used as the solvent for the absorption of the gas mixture.

It is possible with the process disclosed in DE 20 40 219 to separate the different nitrogen oxides, but the process entails the use of large amounts of solvent and/or high pressures for the absorption. At the same time, a further wash tower is needed for the process disclosed in DE 20 40 219 to remove further disruptive components.

WO 2006/032502 discloses a process for purifying a gas mixture comprising dinitrogen monoxide, which comprises at least one absorption of the gas mixture in an organic solvent and subsequent desorption of the gas mixture from the laden organic solvent, and also the adjustment of the content of nitrogen oxides $NO_x$ in the gas mixture to at most 0.5% by volume based on the total volume of the gas mixture. WO 2006/032502 also discloses that the process may comprise a plurality of absorption and desorption steps. WO 2006/032502 discloses only organic solvents as the absorption medium.

DE 10 2005 055588.5 relates to a process for purifying a gas mixture G-0 comprising dinitrogen monoxide, at least comprising the absorption of the gas mixture G-0 in an organic solvent, subsequent desorption of a gas mixture G-1 from the laden organic solvent, absorption of the gas mixture G-1 in water and subsequent desorption of a gas mixture G-2 from the laden water, and to the use of a purified gas mixture comprising dinitrogen monoxide obtainable by such a process as an oxidizing agent for olefins.

EP 06 125 807.5 relates to a process for purifying a gas mixture comprising dinitrogen monoxide, wherein absorption and desorption are effected in aqueous solvent mixtures at particular pH values.

However, with the known processes, small amounts of oxygen which remain in the dinitrogen monoxide can be removed only with difficulty. Specifically traces of oxygen may, however, lead to undesired by-products in subsequent reactions.

For example, in the oxidation of cyclopentene or cyclododecatriene, it has been observed that between 1 and 4 mol of the olefins used are consumed unproductively per mole of oxygen in the dinitrogen monoxide used, i.e. the presence of oxygen in the dinitrogen monoxide can lead to the formation of by-products, for example to the formation of deposits, which can then lead to a blockage of the rector.

Proceeding from this prior art, it was an object of the present invention to provide a process with which the content of oxygen in dinitrogen monoxide-containing streams can be reduced effectively and inexpensively. Dinitrogen monoxide purified in this way is required especially as an oxidizing agent.

BRIEF SUMMARY OF THE INVENTION

This object is achieved in accordance with the invention by a process for purifying a gas mixture comprising dinitrogen monoxide, at least comprising the steps of:
(I) at least partially condensing a gas mixture G-I comprising dinitrogen monoxide to obtain a liquid composition C-1 comprising dinitrogen monoxide,
(II) contacting the composition C-1 with a gas mixture M-1 to obtain a composition C-2 and a gas mixture M-2.

DETAILED DESCRIPTION OF THE INVENTION

One advantage of the process according to the invention is that small traces of oxygen in particular can be removed from the gas mixture comprising dinitrogen monoxide.

The term "gas mixture" as used in the context of the present invention refers to a mixture of two or more compounds which are in the gaseous state at ambient pressure and ambient temperature. At altered temperature or altered pressure, the gas mixture may also be present in another state of matter, for example liquid, and is still referred to as a gas mixture in the context of the present invention.

In the context of the present invention, the composition of the gas mixtures or of the liquefied gas mixtures, unless explicitly stated otherwise, is specified in % by volume. The data relate to the composition of the gas mixtures at ambient pressure and ambient temperature.

In principle, the composition of the mixtures may be determined in the context of the present invention in any way known to those skilled in the art. In the context of the present invention, the composition of the gas mixtures is preferably determined by gas chromatography. However, it may also be determined by means of UV spectroscopy, IR spectroscopy or by wet chemical methods.

In the context of the present invention, a condensation of the gas mixture G-I is performed in step (I).

This affords a liquid composition C-1 comprising dinitrogen monoxide. In the at least partial condensation in step (I), it is additionally possible for an uncondensed portion to be obtained, i.e. a gas mixture G-K.

The process according to the invention further comprises a step (II) wherein the composition C-1 is contacted with a gas mixture M-1 to obtain a composition C-2 and a gas mixture M-2.

The gas mixture G-I may in principle originate from any desired source. For instance, it may be the product of a dinitrogen monoxide synthesis or an offgas stream of another process, which has been concentrated if appropriate.

The condensation in step (I) of the process according to the invention can in principle be effected by any suitable process known to those skilled in the art. In the context of the present invention, the gas mixture G-I is at least partially condensed. According to the invention, from 20 to 99% by weight, preferably from 50 to 90% by weight and most preferably from 60 to 80% by weight of the gas mixture G-I is condensed.

In a further embodiment, the present invention therefore relates to a process for purifying a gas mixture comprising dinitrogen monoxide as described above, wherein from 20 to 90% by weight of the gas mixture G-I is condensed in step (I).

The treatment in step (I) of the process according to the invention affords the liquid composition C-1 in which the proportion of disruptive secondary components, especially oxygen, has been reduced further compared to the gas mixture G-I.

According to the invention, the conditions are especially selected such that dinitrogen monoxide condenses, while the undesired constituents of the gas mixture G-I are condensed only to a minor degree, if at all.

At the same time, in the case of partial condensation, a gaseous mixture G-K is obtained which, as well as dinitrogen monoxide, may comprise further components such as oxygen, nitrogen, carbon dioxide, argon or carbon monoxide.

According to the invention, the gaseous mixture G-K comprises, for example, from 70 to 90% by volume of dinitrogen monoxide, especially from 75 to 85% by volume, more preferably from 78 to 82% by volume. According to the invention, the gaseous mixture G-K further comprises, for example, from 4 to 18% by volume of carbon dioxide, especially from 6 to 16% by volume and more preferably from 8 to 12% by volume of $CO_2$. The gaseous mixture G-K further comprises, for example, from 0.01 to 5% by volume of oxygen, especially from 0.5 to 3% by volume and more preferably from 1.0 to 2.0% by volume of oxygen, and, for example, from 0 to 1% by volume of argon, where the sum of the components of the gaseous mixture G-K adds up to 100% by volume.

Preferably in step (I), the gas mixture G-I is first compressed and then cooled, preferably in two stages. The gas mixture G-I is advantageously compressed to a pressure of from 1 to 35 bar, preferably from 2 to 30 bar, more preferably from 3 to 27 bar. Cooling is preferably effected in two stages, in which case cooled to from 1 to 25° C., preferably to from 8 to 12° V, in the first stage and readily condensable constituents such as water or organic solvents are removed, and then cooled, in the second stage, preferably to from 0 to −70° C., more preferably from −1 to −30° C., especially from −2 to −25° C.

The liquid composition C-1, as well as dinitrogen monoxide, advantageously also comprises carbon dioxide. $CO_2$ has inertizing action and ensures safe operation in the course of processing and especially in the course of storage and further use of the liquid composition C-1. It has been found that, in the case of presence of $CO_2$ as an inert gas in compositions comprising $N_2O$, significantly smaller amounts of carbon dioxide are required compared to other inert gases in order to prevent the self-decomposition capability of dinitrogen monoxide. Small amounts of $CO_2$ are therefore sufficient for inertization of the liquid composition C-1.

According to the invention, the process for purifying a gas mixture comprising dinitrogen monoxide, as well as steps (I) and (II), may also comprise further steps. For instance, it is also possible that the process comprises further steps after step (I) and before step (II).

For example, in the process according to the invention, the composition C-1 can be treated further. In the context of the present invention, it is more particularly possible that there is a further step for concentration of the composition C-1. In principle, all suitable methods known to those skilled in the art for further concentration of the composition C-1 or for removal of impurities, for example of residues of solvent, are possible.

According to the invention, the process comprises especially a further step (II) for removal of impurities from the composition C-1. Preferably, in step (II), the composition C-1 comprising dinitrogen monoxide is contacted with a gas mixture M-1 to obtain a composition C-2 and a gas mixture M-2.

By means of the treatment in step (II) of the process according to the invention, it is possible to remove further impurities which might be disruptive in a further reaction, for example oxygen, from the liquid composition C-1.

The gas mixture M-1 used may in principle be all substances which have a lower boiling point than dinitrogen monoxide or mixtures thereof. Preference is given to using gases which do not react with dinitrogen monoxide, for example nitrogen, helium, neon, argon, krypton, xenon, hydrogen, carbon monoxide, methane and tetrafluoromethane.

Particular preference is given to using nitrogen as gas mixture M-1.

In a further embodiment, the present invention therefore also relates to a process as described above for purifying a gas mixture comprising dinitrogen monoxide, wherein the gas mixture M-1 is selected from the group consisting of nitrogen, helium, neon, argon, krypton, xenon, hydrogen, carbon monoxide, methane and tetrafluoromethane.

For the treatment in step (II), in the context of the present invention, it is possible to use any apparatus suitable for contacting gases and liquids with one another. The examples here include bubble columns, for example operated in cocurrent or countercurrent, with or without random packing or structured packing, in trickle or liquid-phase mode, stirred tanks, for example with sparging stirrers, or the like. The treatment in step (II) can be effected either batchwise or continuously. Preference is given to performing it continuously.

In a further embodiment, the present invention therefore also relates to a process as described above for purifying a gas mixture comprising dinitrogen monoxide, wherein step (II) is performed continuously.

In the context of the present invention, step (II) is especially performed in a bubble column, in which case the bubble column is more preferably operated in countercurrent and is especially preferably provided with a structured packing.

The present invention therefore relates, in a further embodiment, also to a process as described above for purifying a gas mixture comprising dinitrogen monoxide, wherein step (II) is performed in a bubble column.

In a further embodiment, the present invention also relates to a process as described above for purifying a gas mixture comprising dinitrogen monoxide, wherein the bubble column is operated in countercurrent and is more preferably provided with a structured packing.

The process is especially conducted in such a way that, in the countercurrent bubble column, the composition C-1 is introduced at the top and the composition C-2 is withdrawn at the bottom.

The treatment in step (II) is preferably performed at a temperature between −90° C. and +37° C., preferably at a temperature between −80° C. and 0° C. Preference is given to performing the treatment in step (II) at a pressure which is at least as high as the vapor pressure of the liquid composition C-1 at the selected temperature and at not more than 100 bar.

According to the invention, the amount of gas mixture M-1 used must be sufficiently great to achieve the desired oxygen depletion but, on the other hand, as small as possible in order to avoid losses of dinitrogen monoxide. Typically between 5 and 100 mol of gas mixture M-1 are used per mole of oxygen in the liquid composition C-1, preferably between 15 and 30 mol of gas mixture M-1 per mole of oxygen in the liquid composition C-1.

In step (II), a liquid composition C-2 is obtained, whose oxygen content has been reduced further compared to the liquid composition C-1.

According to the invention, the composition C-2 comprises, for example, from 75 to 95% by volume of dinitrogen monoxide, especially from 80 to 90% by volume, more preferably form 82 to 88% by volume. According to the invention, the composition C-2 further comprises, for example, from 4 to 18% by volume of carbon dioxide, especially from 6 to 16% by volume and more preferably from 8 to 12% by volume of $CO_2$. The composition C-2 further comprises, for example, from 0.01 to 1.0% by volume of oxygen, especially from 0.05 to 0.5% by volume and more preferably from 0.1 to 0.4% by volume of oxygen, and, for example, from 0 to 1% by volume of nitrogen, where the sum of the components of the composition C-2 adds up to 100% by volume.

In step (II), a gas mixture M-2 is also obtained, which, in addition to the gas mixture M-1, may comprise further components, for example oxygen.

According to the invention, the gas mixture M-2 comprises, for example, from 70 to 90% by volume of dinitrogen monoxide, especially from 75 to 85% by volume, more preferably from 77 to 82% by volume. According to the invention, the gas mixture M-2 additionally comprises, for example, from 4 to 18% by volume of carbon dioxide, especially from 6 to 16% by volume and more preferably from 8 to 12% by volume of $CO_2$. The gas mixture comprises, for example, from 4 to 18% by volume of nitrogen, especially from 6 to 16% by volume and more preferably from 8 to 12% by volume of nitrogen. The gas mixture M-2 further comprises, for example, from 0.01 to 5% by volume of oxygen, especially from 0.5 to 3% by volume and more preferably from 1.0 to 2.0% by volume of oxygen, and, for example, from 0 to 1% by volume of argon, where the sum of the components of gas mixture M-2 adds up to 100% by volume.

In principle, the gas mixture G-I, in the context of the present invention, may originate from any desired source. According to the invention, it is, however, preferred that the gas mixture G-I is a gas mixture comprising dinitrogen monoxide which has been concentrated beforehand, for example by a process comprising an absorption and desorption in a suitable solvent.

The present invention therefore relates, in a further embodiment, also to a process for purifying a gas mixture comprising dinitrogen monoxide as described above, wherein the gas mixture G-I is obtained by a process comprising the steps of:

(A) treating a gas mixture G-0 comprising dinitrogen monoxide to obtain a gas mixture G-A, at least comprising the steps of
 (i) absorbing the gas mixture G-0 in a solvent mixture S-I to obtain an offgas stream and a composition C-A
 (ii) desorbing a gas mixture G-1 from the composition C-A to obtain a solvent mixture S-I'.

When step (ii) of step (A) is performed directly before step (I) of the process according to the invention, the composition of the gas mixture G-1 corresponds to that of the gas mixture G-I.

In step (A), a gas mixture G-0 comprising dinitrogen monoxide is treated to obtain a gas mixture G-A, step (A) comprising at least steps (i) and (ii). In step (i), the gas mixture G-0 is absorbed in a solvent mixture S-I to obtain an offgas stream and a composition C-A. In step (ii), a gas mixture G-1 is desorbed from the composition C-A to obtain a solvent mixture S-I'.

In the context of the present invention, the gas mixture G-0 is a gas mixture comprising dinitrogen monoxide, which is used in the process according to the invention. The gas mixture G-0 may comprise further components as well as dinitrogen monoxide.

According to the invention, the gas mixture G-0 comprising dinitrogen monoxide used may in principle stem from any source.

When a gas mixture G-0 is used, its content of dinitrogen monoxide is substantially arbitrary, as long as it is guaranteed that the inventive purification is possible.

The $N_2O$-containing gas mixtures which are used as gas mixture G-0 for this process generally have an $N_2O$ content between 2 and 80% by volume of $N_2O$. It further comprises, for example, from 2 to 21% by volume of $O_2$ and up to 30% by volume of $NO_x$ as undesired components. In addition, it may also comprise varying amounts of $N_2$, $H_2$, $CO_2$, CO, $H_2O$, $NH_3$; traces of organic compounds may also be present. For example, the gas mixture G-0 may also comprise from 9 to 13% by volume of $N_2$ and up to 5.5% by volume of $NH_3$. The sum of the components of the gas mixture G-0 adds up to 100% by volume.

In a preferred embodiment of the process according to the invention, a gas mixture G-0 comprising at least 3% by volume of dinitrogen monoxide is used, but preference is given in turn to using mixtures having a dinitrogen monoxide content in the range from 4 to 60% by volume, more preferably in the range from 5 to 25% by volume and especially preferably in the range from 8 to 14% by volume.

In this embodiment, the gas mixture G-0 preferably has an $N_2O$ content of from 8 to 18% by volume, more preferably, for example, 9% by volume, 10% by volume, 11% by volume, 12% by volume, 13% by volume, 14% by volume, 15% by volume, 16% by volume or 17% by volume.

The gas mixture G-0 has, for example, a $CO_2$ content of from 0.1 to 7.5% by volume, preferably from 0.5 to 5% by volume, more preferably from 1 to 2.5% by volume. At the same time, the gas mixture G-0 has, for example, an $O_2$ content of from 1 to 10% by volume, preferably from 2 to 7.5% by volume, more preferably, for example, from 3.0 to 6% by volume. In addition, the gas mixture G-0 may also comprise from 50 to 95% by volume of $N_2$, preferably from 60 to 90% by volume, more preferably from 70 to 85% by volume, and also further components, for example nitrogen oxides or solvent residues. $NO_x$ may, for example, be present in an amount of from 0 to 0.2% by volume, preferably from 0.0001 to 0.15% by volume, more preferably from 0.0005 to 0.1% by volume. The sum of the components of the gas mixture G-0 adds up to 100% by volume.

In a preferred embodiment of the present invention, the gas mixture G-0 comprising dinitrogen monoxide is at least one dinitrogen monoxide-containing offgas of a chemical process. The scope of the present invention also embraces embodiments in which at least two nitrogen monoxide-containing offgases of a single plant serve as the gas mixture comprising dinitrogen monoxide. Equally embraced are embodiments in which at least one dinitrogen monoxide-containing offgas of one plant and at least one further dinitrogen monoxide-containing offgas of at least one further plant serve as the gas mixture comprising dinitrogen monoxide.

Accordingly, the present invention also relates to a process as described above, wherein the gas mixture comprising dinitrogen monoxide is at least one dinitrogen monoxide-containing offgas of at least one industrial process.

The term "gas mixture comprising dinitrogen monoxide" refers in the context of the present invention both to embodiments in which the offgas mentioned is subjected to the inventive purification process in unmodified form and to embodiments in which at least one of the offgases mentioned is subjected to a modification.

The term "modification" as used in this context within the scope of the present invention refers to any suitable process by which the chemical composition of a gas mixture is altered. Accordingly, the term "modification" comprises, inter alia, embodiments in which a dinitrogen monoxide-containing offgas is concentrated with regard to the dinitrogen monoxide content in at least one suitable process. Preference is given to not subjecting the offgas to any modification.

In a further embodiment, the chemical composition of an offgas may also be altered by adding pure dinitrogen monoxide to the offgas.

The gas mixture G-0 comprising $N_2O$ which is used may, for example, be an offgas from an industrial process. It preferably stems from an offgas of a plant for oxidation of alcohols, aldehydes or ketones with nitric acid, for example from an adipic acid plant, dodecanedicarboxylic acid plant or glyoxal plant, from the offgas of a nitric acid plant which uses the above offgas streams as a reactant, from the offgas of a plant for the partial oxidation of $NH_3$ or from the offgas of a plant which uses the gas mixtures generated therein, for example a hydroxylamine plant.

According to the invention, it is also possible to use a mixture of different offgases.

In a more preferred embodiment of the present invention, the at least one dinitrogen monoxide-containing offgas stems from an adipic acid plant, a dodecanedicarboxylic acid plant, a glyoxal plant, a hydroxylamine plant and/or a nitric acid plant, the latter in turn preferably being operated with at least one offgas of an adipic acid plant, of a dodecanedicarboxylic acid plant or of a glyoxal plant.

In a preferred embodiment, the offgas stream of an adipic acid plant is used, in which generally from 0.8 to 1.0 mol of $N_2O$ per mole of adipic acid formed is formed by oxidation of cyclohexanol/cyclohexanone mixtures with nitric acid. As described, for example, in A. K. Uriarte et al., Stud. Surf. Sci. Catal. 130 (2000) p. 743-748, the offgases of adipic acid plants also comprise different concentrations of further constituents including nitrogen, oxygen, carbon dioxide, carbon monoxide, nitrogen oxides, water and volatile organic compounds.

The abovementioned dodecanedicarboxylic acid plant is substantially of an identical plant type.

An example of a typical composition of an offgas of an adipic acid plant or of a dodecanedicarboxylic acid plant is reproduced in the following table:

| Component | Concentrations % by weight |
|---|---|
| $NO_x$ | 19-25 |
| $N_2O$ | 20-28 |
| $N_2$ | 30-40 |
| $O_2$ | 7-10 |
| $CO_2$ | 2-3 |
| $H_2O$ | ~7 |

The offgas stream of an adipic acid plant or of a dodecanedicarboxylic acid plant may be used directly in the process according to the invention.

In a likewise preferred embodiment, the offgas stream of a nitric acid plant is used which is fed fully or partly with offgases comprising dinitrogen monoxide and nitrogen oxides from other processes. In such nitric acid plants, nitrogen oxides are adsorbed and for the most part converted to nitric acid, while dinitrogen monoxide is not converted. For example, such a nitric acid plant may be supplied by nitrogen oxides which are prepared by selective combustion of ammonia and by offgases of an adipic acid plant and/or by offgases of a dodecanedicarboxylic acid plant. It is equally possible to supply such a nitric acid plant solely by offgases of an adipic acid plant and/or by offgases of a dodecanedicarboxylic acid plant.

The offgases of such nitric acid plants always comprise varying concentrations of still further constituents including nitrogen, oxygen, carbon dioxide, carbon monoxide, nitrogen oxides, water and volatile organic compounds.

An example of a typical composition of an offgas of such a nitric acid plant is reproduced in the following table:

| Component | Concentrations % by weight |
|---|---|
| $NO_x$ | <0.1 |
| $N_2O$ | 4-36 |
| $N_2$ | 57-86 |
| $O_2$ | 3-9 |
| $CO_2$ | 1-4 |
| $H_2O$ | ~0.6 |

The offgas stream of a nitric acid plant of this type may be used directly in the process according to the invention.

In a likewise preferred embodiment of the process according to the invention, the offgas stream of a hydroxylamine plant is used, in which, for example, ammonia is initially oxidized with air or oxygen to give NO, and small amounts of dinitrogen monoxide are formed as a by-product. The NO is subsequently hydrogenated with hydrogen to give hydroxylamine. Since dinitrogen monoxide is inert under the hydrogenation conditions, it accumulates in the hydrogen circuit. In preferred process versions, the purge stream of a hydroxylamine plant comprises dinitrogen monoxide in the range from 9 to 13% by volume in hydrogen. This purge stream may be used as such for the inventive purification. It is equally possible to concentrate this stream in a suitable manner with regard to the dinitrogen monoxide content as described above.

Accordingly, the present invention also relates to a process as described above, wherein the gas mixture G-0 is the offgas of an adipic acid plant and/or of a dodecanedicarboxylic acid plant and/or of a glyoxal plant and/or of a hydroxylamine plant and/or of a nitric acid plant operated with the offgas of an adipic acid plant and/or of a dodecanedicarboxylic acid plant and/or of a glyoxal plant.

It is equally possible in the context of the process according to the invention to selectively prepare dinitrogen monoxide for use in the process. Preference is given inter alia to the preparation via the thermal decomposition of $NH_4NO_3$, as described, for example, in U.S. Pat. No. 3,656,899. Preference is likewise further given to the preparation via the catalytic oxidation of ammonia, as described, for example, in U.S. Pat. No. 5,849,257 or in WO 98/25698.

In the absorption in step (i), the gas mixture G-0 is absorbed in a solvent mixture S-I. In the context of the present invention, it is possible in principle to use any method of absorption known to those skilled in the art. This affords an offgas stream and a composition C-A. The composition C-A is then treated further in step (ii). The gas mixture G-1 is desorbed from the composition C-A to obtain a solvent mixture S-I'.

According to the invention, the gas mixture G-1 comprises at least dinitrogen monoxide and may comprise further components.

According to the invention, the solvent mixture S-I used may be any suitable solvent mixture known to those skilled in the art, provided that it is ensured that the gas mixture G-0, especially dinitrogen monoxide, is at least partly absorbed.

In step (A), a gas mixture G-A comprising dinitrogen monoxide is obtained. The gas mixture G-A may additionally comprise further components. When step (A) does not comprise any further steps after step (ii), the composition of the gas mixture G-1 is identical to that of the gas mixture G-A.

In step (I), the gas mixture G-I obtained from step (A) is at least partly condensed to obtain a liquid composition C-1 comprising dinitrogen monoxide and, if appropriate, a gaseous mixture G-K. In the context of the present invention, the liquid composition C-1 comprises dinitrogen monoxide and may comprise further components.

According to the invention, the gaseous mixture G-K comprises, for example, from 70 to 90% by volume of dinitrogen monoxide, especially from 75 to 85% by volume, more preferably from 78 to 82% by volume. According to the invention, the gaseous mixture G-K additionally comprises, for example, from 4 to 18% by volume of carbon dioxide, especially from 6 to 16% by volume and more preferably from 8 to 12% by volume of $CO_2$. The gaseous mixture G-K further comprises, for example, from 0.01 to 5% by volume of oxygen, especially from 0.5 to 3% by volume and more preferably from 1.0 to 2.0% by volume of oxygen, and, for example, from 0 to 1% by volume of argon, where the sum of the components of the gaseous mixture G-K adds up to 100% by volume.

According to the invention, the process may comprise further steps. For example, it is possible in the context of the present invention that further steps are included between steps (A) and (I).

According to the invention, step (A) may also comprise further steps. More particularly, it is possible that step (A) comprises a further absorption of the gas mixture G-1 in a suitable solvent mixture and a further desorption.

In a further embodiment, the present invention therefore relates to a process as described above for purifying a gas mixture comprising dinitrogen monoxide, wherein step (A) additionally comprises steps (iii) and (iv):

(iii) absorbing the gas mixture G-1 in a solvent mixture S-II to obtain an offgas stream and a composition C-B
(iv) desorbing a gas mixture G-2 from the composition C-B to obtain a solvent mixture S-II'.

According to the invention, the solvent mixture S-II used may be any suitable solvent mixture known to those skilled in the art, provided that it is ensured that the gas mixture G-1, especially dinitrogen monoxide, is at least partly absorbed.

When step (A) does not comprise any further steps after step (iv), the composition of gas mixture G-2 is identical to that of gas mixture G-I.

In the context of the present invention, it is also possible that step (A), as well as steps (i) and (ii), or as well as steps (i), (ii), (iii) and (iv), comprises further steps, including further absorptions and desorptions.

For instance, it is possible in the context of the present invention that the process comprises a plurality of steps (i) and (ii) or a plurality of steps (iii) and (iv).

In a further embodiment, the present invention relates to a process as described above for purifying a gas mixture comprising dinitrogen monoxide, wherein step (A) comprises further steps.

In a preferred embodiment, the process according to the invention comprises, in step (A), at least the steps (i) and (ii), and, in a further embodiment, also steps (iii) and (iv), wherein the solvent mixtures S-I and S-II are used.

According to the invention, the solvent mixtures S-I and/or S-II used may be any suitable solvent mixture known to those skilled in the art, provided that it is ensured that especially dinitrogen monoxide is absorbed.

Suitable solvent mixtures S-I and S-II for the absorption in step (i) or (iii) of step (A) are those which have a better solubility for $N_2O$ and preferably also $CO_2$ as an inert component than for the undesired components of the incoming reactant gas G-0.

According to the invention, the solvent mixtures S-I and/or S-II used may be organic solvents or aqueous solvent mixtures. In a further embodiment, the present invention therefore relates to a process as described above for purifying a gas mixture comprising dinitrogen monoxide, wherein the solvent mixture S-I or the solvent mixture S-II or the solvent mixture S-I and the solvent mixture S-II is/are selected from the group consisting of organic solvents and aqueous solvent mixtures.

According to the invention, the organic solvents used may be any solvents in which the ratio between $N_2O$ solubility (in mol/mol of solvent) and the solubility of the undesired secondary components under the conditions existing in the absorber (this ratio is referred to hereinafter as γ) is at least 5. This ratio may be determined for each individual component present in the gas mixture. Preferred organic solvents have, for example at 30° C., a $\gamma_{O2}$ value of from 6 to 30, preferably from 9 to 25, and a $\gamma_{N2}$ value of greater than 10, preferably of greater than 15, in particular of greater than 20.

Examples of suitable organic solvents are, for example, aliphatic hydrocarbons, preferably having at least 5 carbon atoms, more preferably having at least 8 carbon atoms, substituted or unsubstituted aromatic hydrocarbons, esters, ethers, amides, lactones, lactams, nitriles, alkyl halides, olefins or mixtures of these solvents.

According to the invention, preference is given to solvents which have a boiling point at standard pressure of at least 100° C., since this reduces the solvent losses both in the offgas stream of the absorber and of the desorber.

In addition, solvents suitable in accordance with the invention simultaneously have a good solubility for dinitrogen monoxide. The solubility is specified by the ratio between the partial pressure of $N_2O$ in the gas phase and the molar proportion of $N_2O$ in the liquid phase (Henry coefficient, $H_{N2O}$), i.e. a small value means a high solubility of dinitrogen monoxide in the solvent. This ratio for an organic solvent used in the first step at 30° C. is preferably less than 1000, more preferably less than 750, particularly preferably less than 500, in particular less than 150.

Suitable solvents also include N-methylpyrrolidone, dimethylformamide, dimethyl sulfoxide, propylene carbonate, sulfolane, N,N-dimethylacetamide or cyclopentane. Particular preference is given in the context of the present invention, for example, to toluene, nitrobenzene, 1,2-dichlorobenzene, tetradecane, for example a technical-grade mixture of saturated hydrocarbons having predominantly 14 carbon atoms, and dimethyl phthalate.

In a preferred embodiment, the present invention therefore relates to a process for purifying a gas mixture comprising dinitrogen monoxide as described above, wherein the organic solvent is selected from the group consisting of toluene, nitrobenzene, 1,2-dichlorobenzene, tetradecane and dimethyl phthalate.

According to the invention, it is likewise possible to use aqueous solvent mixtures as solvent mixture S-I and/or S-II. In principle, the above remarks apply for the suitability of the aqueous solvent mixtures for the process according to the invention. In particular, the solvent mixtures S-I and/or S-II used may be solvent mixtures at least comprising 50% by weight of water based on the overall solvent mixture. It is also possible in the context of the present invention that the pH of the solvent mixture used is set within a particular range. According to the invention, a suitable pH for an aqueous solvent mixture is, for example, in the range from 2.0 to 8.0. It is also possible in accordance with the invention that the pH of the aqueous solvent mixtures S-I or S-II used in the individual absorption steps is varied.

In the context of this application, the pH is measured with a commercially available glass electrode which has been calibrated beforehand against a buffer of known pH. All pH data are based on a measurement with a calibrated and temperature-compensated glass electrode. If the calibration temperature differs from the measurement temperature, a temperature compensation is used. This definition and this method correspond to the currently valid IUPAC recommendation (R. P. Buck et al., *Pure Appl. Chem.* (2002) 74(11), p. 2169-2200 and especially section 11 thereof).

Water has a high selectivity for the desired components, especially dinitrogen monoxide and carbon dioxide. At the same time, the absolute solubility of dinitrogen monoxide in water is sufficient to achieve further concentration. Water as a solvent has the advantage that, even under pressure in the presence of concentrated dinitrogen monoxide, no safety problems occur. At the same time, no contamination of the gas mixture obtained from the desorption with an organic solvent can occur, which would necessitate additional purification steps.

According to the invention, both solvent mixture S-I and S-II may be an organic solvent mixture or an aqueous solvent mixture. According to the invention, it is possible that the solvent mixture S-I used is an organic solvent and the solvent mixture S-II used is an aqueous solvent mixture. It is equally possible that the solvent mixture S-I used is an aqueous solvent mixture and the solvent mixture S-II an organic solvent. In the context of the present invention, both solvent mixture S-I and solvent mixture S-II are preferably an aqueous solvent mixture.

It is additionally preferred that, when the solvent mixture S-I and/or S-II used is an aqueous solvent mixture, the pH of the aqueous solvent mixture is set within a particular range.

By virtue of the inventive selection of the pH of the solvent mixture S-I and solvent mixture S-II, almost complete depletion of $NO_x$ is achieved. This makes a separate removal of $NO_x$, for example by means of DeNOx or SCR-DeNOx, superfluous. As a result, in the process according to the invention, there is, for example, also no risk of contamination of the product stream with $NH_3$, which is used as a reducing agent for the DeNOx stage.

As a result of the controlled selection, which is preferred in accordance with the invention, of the pH of the solvent mixture S-I and of the solvent mixture S-II, it is possible especially to achieve good depletion of $NO_x$ with only a minimal change in the carbon dioxide content.

The solvent mixtures S-I and S-II used in accordance with the invention have, at the pH preferred in accordance with the invention, a high selectivity for the desired components, especially dinitrogen monoxide and carbon dioxide. At the same time, the absolute solubility of dinitrogen monoxide in the solvent mixture S-I or S-II used in accordance with the invention is sufficient to achieve concentration. The solvent mixture S-I or S-II used in accordance with the invention has the advantage that, even under pressure in the presence of concentrated dinitrogen monoxide, no safety problems occur.

According to the invention, the pH of the aqueous solvent mixture in the absorption may preferably be in the range from 3.5 to 8.0. At this pH, according to the invention, there is a good absorption of dinitrogen monoxide and carbon dioxide in the solvent mixture, while other gases which may be present in the gas mixture G-0 are absorbed to a small degree, if at all. The pH is preferably within a range from 5.0 to 7.5, more preferably within a range from 6.0 to 7.0.

According to the invention, the pH is measured before or during the contacting of the gas mixture with the aqueous solvent mixture and then, for example, the pH is adjusted by suitable measures. It is equally possible in accordance with the invention that no measures are needed to adjust the pH.

In principle, the pH can, in accordance with the invention, be adjusted by all measures known to those skilled in the art. Suitable measures for adjusting the pH are, for example, addition of an acid or alkali or addition of further solvents.

For example, the pH of the aqueous solvent mixture is measured before or after the absorption and the pH is set within the inventive range by suitable measures. According to the invention, the pH can be measured continuously or discontinuously.

When the pH values of solvent mixture S-I and of solvent mixture S-II are adjusted, the pH of solvent mixture S-I and of solvent mixture S-II can be adjusted independently of one another. According to the invention, it is also possible that only the pH of solvent mixture S-I or of solvent mixture S-II is adjusted. However, it is also possible in accordance with the invention for the pH of solvent mixture S-I and of solvent mixture S-II to be adjusted within the same range.

In the context of the present invention, an aqueous solvent mixture is understood to mean a solvent mixture at least comprising 50% by weight of water, for example from 50 to 100% by weight of water, preferably at least 60% by weight of water, especially at least 70% by weight of water, more preferably at least 80% by weight of water, for example at least 90% by weight of water. The aqueous solvent mixture preferably comprises at least 90% by weight of water, based in each case on the overall aqueous solvent mixture.

The present invention therefore also relates to a process as described above for purifying a gas mixture comprising dinitrogen monoxide, wherein the solvent mixture S-I or the solvent mixture S-II or the solvent mixture S-I and the solvent mixture S-II comprise(s) at least 90% by weight of water, based in each case on the overall solvent mixture.

According to the invention, the aqueous solvent mixture, in addition to water, may also comprise other polar water-miscible solvents, for example glycols. In addition, the aqueous solvent mixture, as well as water, may also comprise dissolved salts, for example salts of the alkali metals or alkaline earth metals, especially hydroxides, hydrogencarbonates, carbonates, nitrates, nitrites, sulfates, hydrogenphosphates or phosphates.

According to the invention, the content of salts in the aqueous solvent mixture is less than 5% by weight, preferably less than 2.5% by weight, especially less than 2.0% by weight. The content of salts in the aqueous solvent mixture is, for example, from 0.0001 to 5% by weight, preferably from 0.001 to 2.5% by weight, especially from 0.01 to 2.0% by weight.

According to the invention, the content of salts in the aqueous solvent mixture is preferably controlled by continuously or discontinuously replacing a portion of the solvent mixture laden with salts with an appropriately adjusted amount of fresh solvent mixture.

According to the invention, the pH of the aqueous solvent mixture can be adjusted by means of any method known to those skilled in the art. More particularly, the pH can be adjusted by adding a base to the aqueous solvent mixture.

In principle, the base used may be any conceivable compound whose pH, as a 1% by weight solution in water, is >8.0. Preference is given in accordance with the invention to using strong inorganic bases, especially hydroxides, carbonates, hydrogen-carbonates or phosphates of alkali metals or alkaline earth metals. Particular preference is given to using NaOH, KOH, $Na_2CO_3$, $NaHCO_3$, $Na_3PO_4$, $K_3PO_4$. Additionally preferred is the use of the bases in the form of a concentrated aqueous solution.

In the context of the present invention, suitable concentration ranges are, for example, from 10 to 60% aqueous solutions, preferably from 20 to 55% aqueous solutions, more preferably from 25 to 50% aqueous solutions, for example 30% aqueous solutions, 35% aqueous solutions, 40% aqueous solutions, 45% aqueous solutions or 50% aqueous solutions.

Particular preference is given in accordance with the invention to the use of an aqueous NaOH solution as the base.

In a preferred embodiment of the present invention, the base used is a from 25 to 50% aqueous NaOH solution.

For example, the pH of the aqueous solvent mixture is adjusted by adding a base selected from the group consisting of alkali metal hydroxides, alkali metal carbonates, alkali metal hydrogencarbonates, alkali metal phosphates, alkaline earth metal hydroxides, alkaline earth metal carbonates, alkaline earth metal hydrogencarbonates and alkaline earth metal phosphates.

In step (i), according to the invention, there is an at least partial absorption of the gas mixture G-0 in a solvent mixture S-I to obtain a composition C-A and an offgas stream depleted of the absorbed gases.

In the context of the present invention, a depleted offgas stream is understood to mean a gas stream which comprises the gases not absorbed in the absorption in the solvent mixture S-I or S-II.

The composition C-A comprises the solvent mixture S-I and the gases absorbed therein.

When the solvent mixture S-I used is water, the composition C-A comprises, for example, from 90.0 to 99.9999% by weight of water, especially from 95.0 to 99.999% by weight and preferably from 98.0 to 99.99% by weight of water; for example from 0.01 to 0.25% by weight of dinitrogen monoxide, especially from 0.05 to 0.2% by weight and preferably from 0.1 to 0.15% by weight of dinitrogen monoxide; for example from 0.0001 to 0.1% by weight of carbon dioxide, especially from 0.001 to 0.05% by weight of carbon dioxide; for example from 0.0001 to 0.1% by weight of nitrogen, especially from 0.001 to 0.05% by weight of nitrogen; for example from 0.05 to 1.5% by weight of sodium nitrite, especially from 0.1 to 1.0% by weight and preferably from 0.25 to 0.75% by weight of sodium nitrite; for example from 0.05 to 1.5% by weight of sodium nitrate, especially from 0.1 to 1.0% by weight and preferably from 0.25 to 0.75% by weight of sodium nitrate; for example from 0.0001 to 0.1% by weight of sodium hydrogencarbonate, especially from 0.001 to 0.05% by weight of sodium hydrogencarbonate; and traces of oxygen and argon. The sum of the components of composition C-A adds up to 100% by weight.

According to the invention, the depleted offgas stream comprises, for example, from 0.1 to 2.0% by volume of argon, especially from 0.25 to 1.5% by volume and preferably from 0.5 to 1.0% by volume of argon; for example from 1.0 to 10% by volume of oxygen, especially from 2.5 to 7.5% by volume and preferably from 4.0 to 6.0% by volume of oxygen; for example from 1.0 to 10% by volume of dinitrogen monoxide, especially from 2.5 to 7.5% by volume and preferably from 4.0 to 6.0% by volume of dinitrogen monoxide; for example from 70 to 99.9% by volume of nitrogen, especially from 75 to 95% by volume and preferably from 80 to 90% by volume of nitrogen; for example from 0.01 to 0.5% by volume of carbon monoxide, especially from 0.05 to 0.25% by volume and preferably from 0.08 to 0.1% by volume of carbon monoxide; for example from 0.1 to 1.5% by volume of carbon dioxide, especially from 0.25 to 1.0% by volume and preferably from 0.5 to 0.75% by volume of carbon dioxide; for example from 0.1 to 1.5% by volume of water, especially from 0.25 to 1.0% by volume and preferably from 0.5 to 0.75% by volume of water. The sum of the components of the offgas stream adds up to 100% by volume.

Preference is given to performing step (i) of the process according to the invention continuously. In the context of the present invention, this means that the solvent mixture S-I and the gas mixture G-0 are contacted continuously, which continuously forms the composition C-A and the depleted offgas stream.

According to the invention, in the absorption in step (i), preferably dinitrogen monoxide and carbon dioxide are absorbed. According to the invention, it is also possible, for example, for nitrogen, oxygen and argon to be absorbed. Nitrogen oxides $NO_x$ are also absorbed in step (i).

In a preferred embodiment, the process according to the invention further comprises a step (ii) in which a gas mixture G-1 is desorbed from the composition C-A to obtain a solvent mixture S-I'.

In step (ii), preferably dinitrogen monoxide and carbon dioxide are desorbed from the composition C-A.

As well as the solvent mixture S-I used, the solvent mixture S-I' also comprises as yet undesorbed gases and conversion products.

For example, in the case that the solvent mixture S-I used with a particular adjusted pH in the process according to the invention and the pH is adjusted by adding an alkali, especially sodium hydroxide solution, the solvent mixture S-I' comprises, in accordance with the invention, for example from 90.0 to 99.9999% by weight of water, especially from 95.0 to 99.999% by weight and preferably from 98.0 to 99.99% of water; for example from 0.001 to 0.1% by weight of dinitrogen monoxide, for example from 0.05 to 1.5% by weight of sodium nitrite, especially from 0.1 to 1.0% by weight and preferably from 0.25 to 0.75% by weight of sodium nitrite; for example from 0.05 to 1.5% by weight of sodium nitrate, especially from 0.1 to 1.0% by weight and preferably from 0.25 to 0.75% by weight of sodium nitrate; for example from 0.0001 to 0.1% by weight of sodium hydrogencarbonate, especially from 0.001 to 0.05% by weight of sodium hydrogencarbonate. The solvent mixture S-I' may additionally also comprise further compounds. The sum of the components of the solvent mixture S-I' adds up to 100% by weight.

In the context of the present invention, the gas mixture G-1 has, for example, an $N_2O$ content of from 40 to 80% by volume, preferably from 45 to 75% by volume, especially from 50 to 65% by volume, more preferably, for example, 51% by volume, 52% by volume, 53% by volume, 54% by volume, 55% by volume, 56% by volume, 57% by volume, 58% by volume, 59% by volume, 60% by volume, 61% by volume, 62% by volume, 63% by volume, 64% by volume or 65% by volume.

The gas mixture G-1 has, for example, a $CO_2$ content of from 5 to 15% by volume, preferably from 6 to 12% by volume, more preferably, for example, 7% by volume, 9% by volume, 10% by volume or 11% by volume. At the same time, the gas mixture G-1 has, for example, an $O_2$ content of from 1.0 to 4.0% by volume, preferably from 1.5 to 3.5% by volume, more preferably from 2.5 to 3.1% by volume, for example 2.6% by volume, 2.7% by volume, 2.8% by volume, 2.9% by volume or 3.0% by volume. In addition, the gas mixture G-1 may also comprise from 20 to 40% by volume of $N_2$, preferably from 20 to 35% by volume, and also further components, for example nitrogen oxides. $NO_x$ may be present, for example, in an amount of from 0 to 0.1% by volume, preferably from 0.0001 to 0.01% by volume, more preferably from 0.0002 to 0.05% by volume. The sum of the components of the gas mixture G-1 adds up to 100% by volume. The gas mixture G-1 may additionally comprise from 0 to 10% by volume of water, especially from 2 to 8% by volume and preferably from 4 to 6% by volume of water.

According to the invention, step (A) may comprise further steps, especially a further absorption and desorption in a suitable solvent according to steps (iii) and (iv). In steps (iii) and (iv), there is an absorption of the gas mixture G-1 in a suitable solvent mixture S-II and a subsequent desorption of the gas mixture G-2.

In the absorption in step (iii), there is, according to the invention, an absorption in a solvent mixture S-II to obtain a composition C-B and an offgas stream depleted of the absorbed gases.

The composition C-B comprises the solvent mixture S-II and the gases absorbed therein.

When the solvent mixture S-II used is water, the composition C-B comprises, for example, from 90.0 to 99.9999% by weight of water, especially from 95.0 to 99.999% by weight and preferably from 98.0 to 99.99% by weight of water; for example from 0.01 to 2.5% by weight of dinitrogen monoxide, especially from 0.1 to 1.5% by weight and preferably from 0.5 to 1.0% by weight of dinitrogen monoxide; for example from 0.001 to 0.5% by weight of carbon dioxide, especially from 0.01 to 0.25% by weight of carbon dioxide; for example from 0.0001 to 0.1% by weight of nitrogen, especially from 0.001 to 0.05% by weight of nitrogen; and traces of oxygen and argon. The sum of the components of the composition C-B adds up to 100% by weight.

Preference is given to performing step (iii) of the process according to the invention continuously. In the context of the present invention, this means that the solvent mixture S-II and the gas mixture G-1 are contacted continuously, which continuously forms the composition C-B and the depleted offgas stream.

Preference is given to performing steps (i) and (iii) of the process according to the invention continuously.

According to the invention, in the absorption in step (iii), preferably dinitrogen monoxide and carbon dioxide are absorbed. Nitrogen oxides $NO_x$ remaining in the gas mixture G-1 are preferably also absorbed in step (iii).

According to the invention, preferably from 60 to 80% of the entering gas stream are absorbed in step (iii).

In a preferred embodiment, the process according to the invention preferably further comprises a step (iv) in which a gas mixture G-2 is desorbed from the composition C-B to obtain a solvent mixture S-II'.

In step (iv), preference is given to desorbing dinitrogen monoxide and carbon dioxide from the composition C-B.

As well as the solvent mixture S-II used, the solvent mixture S-II' comprises as yet undesorbed gases and conversion products.

The resulting gas mixture G-2 comprises at least 50% by volume of $N_2O$, more preferably at least 60% by volume of $N_2O$ and most preferably at least 75% by volume of $N_2O$. Typically, gas mixture G-2 comprises up to 99% by volume of $N_2O$, especially up to 97% by volume of $N_2O$, for example up to 96% by volume of $N_2O$, up to 95% by volume of $N_2O$, up to 94% by volume of $N_2O$, up to 93% by volume of $N_2O$, up to 92% by volume of $N_2O$, up to 91% by volume of $N_2O$, up to 90% by volume of $N_2O$ or else up to 85% by volume of $N_2O$.

In the context of the present invention, the gas mixture G-2 has, for example, an $N_2O$ content of from 60 to 95% by volume, preferably from 70 to 90% by volume, especially from 75 to 85% by volume, more preferably, for example, 76% by volume, 77% by volume, 78% by volume, 79% by volume, 80% by volume, 81% by volume, 82% by volume, 83% by volume, 84% by volume or 85% by volume.

The gas mixture G-2 has, for example, a $CO_2$ content of from 1 to 20% by volume, preferably from 5 to 15% by volume, more preferably, for example, 6% by volume, 7% by volume, 8% by volume, 9% by volume, 10% by volume, 11% by volume, 12% by volume, 13% by volume or 14% by volume. At the same time, the gas mixture G-2 has, for example, an $O_2$ content of from 0.01 to 5.0% by volume, preferably from 0.1 to 2.5% by volume, more preferably, for example, from 0.2 to 1.0% by volume. In addition, the gas mixture G-2 may also comprise from 0.1 to 10% by volume of $N_2$, preferably from 0.5 to 5% by volume, and also further components, for example nitrogen oxides or solvent residues. At the same time, the gas mixture G-2 comprises less than 1% by volume of $O_2$, especially less than 0.5% by volume of $O_2$, less than 0.5% by volume of $NO_x$. $NO_x$ may be present, for example, in an amount of from 0 to 0.1% by volume, preferably from 0.0001 to 0.01% by volume, more preferably from 0.0002 to 0.02% by volume. The sum of the components of the gas mixture G-2 adds up to 100% by volume.

When step (A) comprises no further steps after step (iv), the composition of gas mixture G-I corresponds to the composition of gas mixture G-2.

The absorption in step (i) or (iii) in step (A) of the process according to the invention can in principle be effected by all methods known to those skilled in the art. More particularly, the absorption in the solvent mixture can be brought about by increasing the pressure of the reactant gas or by lowering the temperature of the solvent mixture or by a combination of the measures stated.

In step (i) or (iii) of the process according to the invention, preference is given to first compressing the gas mixture, for example to a pressure of from 10 to 35 bar, preferentially from 13 to 30 bar, preferably from 14 to 25 bar. Subsequently, the compressed gas mixture is preferably contacted at this pressure with the solvent mixture S-I in step (i) or in the solvent mixture S-II in step (iii).

The present invention therefore also relates to a process as described above for purifying a gas mixture G-0 comprising dinitrogen monoxide, wherein the pressure in the absorption in step (i) or (iii) or (i) and (iii) is within a range from 10 to 35 bar.

According to the invention, the absorption in step (i) and step (iii) is effected in equipment (absorbers) in which a gas-liquid phase interface is generated, through which mass and heat transfer between the phases is enabled, and which are provided if required with internal or external equipment for heat supply and/or heat removal.

The phases within the absorber can be conducted in cocurrent, in countercurrent, or in a combination thereof.

According to the invention, the absorption can be effected in one or more stages, preferably in one stage. In the absorption, the absorber used is preferably a device with a plurality of theoretical plates, especially from 2 to 8 theoretical plates, more preferably from 3 to 6.

Possible embodiments of the absorber are in each case columns with trays, for example bubble-cap trays or sieve trays, columns with structured internals, for example structured packings, columns with unstructured internals, for example random packings, or apparatus in which the liquid phase is present in dispersed form, for example as a result of spraying in nozzles, or a combination thereof.

The desorption of the gas mixture G-1 or G-2 from the composition C-A or composition C-B in step (ii) or (iv) of the process according to the invention can be brought about by lowering the pressure over the solvent mixture, increasing the temperature of the solvent mixture, or by stripping with solvent vapor, or a combination thereof.

The demands on the equipment (desorbers) for the desorption of the gas mixture G-1 or G-2 from the composition C-A or composition C-B, and the conduction of the phases, are analogous to those in the absorber, i.e. suitable equipment is that in which a gas-liquid phase interface is generated, through which heat and mass transfer between the phases is enabled, and which are provided if required with internal or external equipment for heat supply and/or heat removal.

According to the invention, the desorption can be performed in one or more stages.

Possible embodiments of the desorber are a simple (flash) vessel and columns.

A preferred embodiment of the present invention in which the absorption, i.e. the contacting with the solvent mixture, and the desorption are combined in one apparatus is, for example, the dividing wall column. In this column, the contacting, and the associated absorption, and the desorption are conducted in countercurrent in a plurality of stages by varying the temperature, combined with stripping with solvent vapor. Both in (i) and (ii) and in (iii) and (iv), the absorption and desorption apparatus can be combined, especially in a dividing wall column.

In a preferred embodiment, the present invention therefore relates to a process as described above, wherein steps (i) and (ii) or steps (iii) and (iv) or steps (i) and (ii) and steps (iii) and (iv) are performed in a dividing wall column.

In a particularly preferred embodiment of the invention, in step (i), the gas mixture G-0 comprising $N_2O$ is first contacted under elevated pressure $p_{abso}$ with the solvent mixture S-I in an absorption column operated in countercurrent and with random packing, which can result in absorption, and a composition C-A is obtained. In step (ii), the composition C-A, in this embodiment, is transferred into a vessel in which the composition C-A is decompressed to a lower pressure $p_{deso} < p_{abso}$. The process is preferably conducted virtually isothermally with a temperature difference between absorption and desorption temperature of not more than 20 K, preferably not more than 15 K, especially not more than 10 K. The absorption pressure here is from 1 to 100 bar, preferably from 5 to 65 bar, especially from 10 to 40 bar, preferably from 10 to 35 bar, more preferably from 13 to 30 bar, even more preferably from about 14 to 25 bar, and the desorption pressure from 0.1 to 2 bar absolute, preferably from 0.5 to 1.5 bar absolute, more preferably from 1.0 to 1.2 bar absolute.

Preference is likewise given, in step (iii), to first contacting the gas mixture G-1 under elevated pressure $p_{abso}$ with a solvent mixture S-II in an absorption column operated in countercurrent and with random packing to obtain the composition C-B. In step (iv), composition C-B is transferred to a vessel in which the composition C-B is decompressed to a lower pressure $p_{deso} < p_{abso}$. The process is preferably likewise conducted virtually isothermally with a temperature difference between the absorption and desorption temperatures of not more than 20 K, preferably not more than 15 K, especially not more than 10 K. The absorption pressure here is from 1 to 100 bar, preferably from 5 to 65 bar, especially from 10 to 40 bar, preferably from 10 to 35 bar, more preferably from 13 to 30 bar, even more preferably from about 14 to 25 bar, and the desorption pressure from 0.1 to 2 bar absolute, preferably from 0.5 to 1.5 bar absolute, more preferably from 1.0 to 1.2 bar absolute.

In addition to steps (i), (ii), (iii) and (iv), step (A) of the process according to the invention may also comprise further steps. For example, the process may also comprise a further treatment of the gas mixture G-1 between steps (ii) and (iii). Such treatments comprise, for example, a change in the temperature or a change in the pressure or a change in the temperature and in the pressure.

For example, the composition of a gas mixture may change, for example through condensation of one of the components. These components may, for example, be water or another compound present in the solvent mixture S-I, preferably a solvent which is used for step (i) in the solvent mixture S-I in the process according to the invention.

According to the invention, it is possible that further components are removed from the gas mixture G-1 or G-2. For example, it is possible that traces of water, which may be present in the gas mixture G-2 in step (iv) after the desorption, are removed from the gas mixture G-2 by compression and subsequent cooling.

In this case, the gas mixture G-2 is advantageously compressed to a pressure of from 1 to 35 bar, preferably from 2 to 30 bar, more preferably from 3 to 27 bar. Cooling is preferably effected subsequently, preferably to from 1 to 25° C., more preferably from 3 to 20° C., especially from 4 to 15° C., more preferably from 8 to 12° C.

In an advantageous embodiment of the process according to the invention, it is also possible that gas mixtures or solvent mixtures are recycled into the process according to the invention, in order to reduce yield losses.

According to the invention, it is possible, for example, that the gas mixture M-2 is recycled into a stage of the process. In such an embodiment, traces of dinitrogen monoxide which are present in gas mixture M-2 can be recycled into the process in order to avoid yield losses.

In a further embodiment, the present invention therefore also relates to a process as described above for purifying a gas mixture comprising dinitrogen monoxide, wherein the gas mixture M-2 is recycled into step (A).

As described above, the gas mixture M-2 is preferably recycled into step (A) of the process according to the invention. In this case, in the context of the present invention, the gas mixture M-2 is mixed with another gas mixture. Preference is given to recycling the gas mixture M-2 into step (A) in such a way that recovery of the dinitrogen monoxide which may be present in gas mixture M-2 is possible. It is therefore preferred in the context of the present invention that the gas mixture M-2 is mixed with a gas mixture which is set to an absorption, especially with the gas mixture G-0 or gas mixture G-1. It is thus preferred in the context of the present invention to recycle gas mixture M-2 into step (i) or into step (iii) of step (A).

In a further embodiment, the present invention therefore also relates to a process as described above for purifying a gas mixture comprising dinitrogen monoxide, wherein the gas mixture M-2 is recycled into step (i) or into step (iii) of step (A).

The pressure in the individual steps of the process according to the invention is preferably selected such that no pump or compressor is required in order to recycle the gas mixture M-2 into step (A). Accordingly, it is preferred that step (II) is performed at a pressure which is, for example, from 0.2 to 5 bar higher than the pressure in step (i) or in step (iii).

In the process according to the invention, the proportion of oxygen in the composition obtained can be reduced significantly. More particularly, in the preferred embodiment comprising the recycling of the gas mixture M-2, this is possible in accordance with the invention without reducing the yield of dinitrogen monoxide.

The liquid composition C-2 which comprises dinitrogen monoxide and is obtained by the process according to the invention can in principle be used for all applications in which pure dinitrogen monoxide streams or dinitrogen monoxide streams admixed with inert gas are typically used. More particularly, the composition C-2 is suitable, for example, for the oxidation of methanol to formaldehyde, as described, for example, in EP-A 0 624 565 or DE-A 196 05 211. The present invention therefore also relates to the use of the liquid composition C-2 which comprises dinitrogen monoxide and is obtainable by a process according to the invention as an oxidizing agent for methanol.

The process according to the invention affords liquid compositions comprising dinitrogen monoxide which have a particularly low proportion of disruptive secondary components. This is especially advantageous for use as an oxidizing agent, since, as a result of the low proportion of disruptive secondary components, barely any side reactions occur and thus particularly pure products can be obtained in an oxidation. Liquid composition C-2 preferably comprises, after the inventive purification, not only dinitrogen monoxide but also carbon dioxide in suitable amounts.

The liquid composition C-2 purified in accordance with the invention comprises preferably from 50 to 99.0% by volume of dinitrogen monoxide, from 1 to 20% by volume of carbon dioxide and from 0 to 25% by volume of further gases. The percentages by volume specified are based in each case on the overall composition C-2. The sum of the individual components of the composition C-2 adds up to 100% by volume.

The composition C-2 purified in accordance with the invention preferably comprises from 60 to 95% by volume of dinitrogen monoxide, especially from 70 to 90% by volume and more preferably from 75 to 89% by volume of dinitrogen monoxide.

The composition C-2 purified in accordance with the invention further comprises from 1 to 20% by volume of carbon dioxide. The composition C-2 preferably comprises from 5 to 15% by volume of carbon dioxide, especially from 6 to 14% by volume of carbon dioxide.

The composition C-2 preferably comprises from 2 to 25% by volume of further gases and more preferably from 0 to 5% by volume. The composition C-2 purified in accordance with the invention may comprise one or more further gases, the amount specified being based on the sum of the gases present. The composition C-2 may comprise, for example, traces of oxygen, nitrogen and water.

It has been found that, in the presence of $CO_2$ as an inert gas in liquefied gas mixtures comprising $N_2O$, compared to other inert gases, significantly smaller amounts of the inert gas, i.e. carbon dioxide, are required to ensure safe operation, for example to prevent self-decomposition of dinitrogen monoxide.

The present invention therefore also relates to the use of a liquid composition C-2 obtainable by a process according to the invention as described above as an oxidizing agent, especially as an oxidizing agent for olefins.

Suitable olefins are, for example, open-chain or cyclic olefins having one or more double bonds. Preference is further given to cyclic olefins having one or more double bonds, for example cyclopentene, cyclohexene, cycloheptene, cyclooctene, cyclodecene, cycloundecene, cyclododecene, 1,4-cyclohexadiene, 1,6-cyclodecadiene, 1,6,11-cyclopentadecatriene, 1,5,9,13-cyclohexadecatetraene or 1,5,9-cyclododecatriene.

In a preferred embodiment, the present invention therefore also relates to use as described above as an oxidizing agent for olefins, wherein the olefin is selected from the group consisting of cyclopentene, cyclododecene and 1,5,9-cyclododecatriene.

The enriched and purified $N_2O$-containing liquid composition C-2 is very particularly suitable for oxidizing olefins to ketones. For this purpose, the liquid composition C-2 can preferably be reacted directly with the olefin.

For such applications, it is advantageous when the proportion of insert gases in the liquid composition C-2 is at a minimum, since the reactor volume is otherwise unnecessarily enlarged.

For the inventive use as an oxidizing agent, especially for olefins, the oxidation can generally be effected by all process regimes in which the oxidation, especially of the olefin, takes place. More particularly, both continuous process regimes and methods of reaction and batch reactions are possible. According to the invention, the reaction conditions for the oxidation are selected such that a reaction takes place. Pressure and temperature can be selected accordingly.

The pressure is preferably within a range up to 500 bar, for example from 1 to 320 bar, preferably from 10 to 300 bar, especially from 90 to 280 bar. The temperature is preferably within a range from 180 to 320° C., for example from 200 to 300° C., especially from 240 to 290° C.

The oxidation can be performed in the presence of a suitable solvent. According to the invention, however, it is equally possible to perform the oxidation without the addition of a solvent.

According to the invention, preference is given to conducting the oxidation, through suitable selection of the pressure and of the temperature, such that no gas phase occurs in the reaction zone.

The invention will be illustrated in detail hereinafter with reference to examples.

EXAMPLES

Example 1

10 kg/h of liquid dinitrogen monoxide at −13° C., in which 1320 ppm by weight of oxygen were present in dissolved form, was fed at a temperature of −13° C. and a pressure of 26 bar into the top of a well-insulated pilot column of internal diameter 30 mm, which was equipped with an approx. 500 mm-high bed of random packing consisting of Raschig rings of diameter 0.5 inch. The column was operated in trickle mode, which means that liquid arriving at the bottom of the column was discharged under level control, and the liquid level was below the bed of random packing. Below the bed of random packing, gaseous nitrogen was introduced into the column in order to remove the oxygen dissolved in the liquid dinitrogen monoxide by stripping in countercurrent. The $O_2$-laden stripping gas was removed at the top of the column under pressure control.

In the course of operation, the amount of nitrogen was varied and the total amount of liquid dinitrogen monoxide leaving at the bottom was measured for each setting. A sample thereof was also taken in each case to determine the oxygen content.

The following results were achieved:

| Example | Nitrogen feed l/h | Bottom product kg/h | $O_2$ dissolved in the bottom product ppm by wt. | Spec. consumption of $N_2$ used/$O_2$ removed mol/mol |
| --- | --- | --- | --- | --- |
| 1 | 2 | 9.40 | 550 | 5.2 |
| 2 | 4 | 9.11 | 256 | 10.5 |
| 3 | 6 | 8.87 | 102 | 15.7 |
| 4 | 8 | 8.83 | 73 | 20.9 |
| 5 | 10 | 8.87 | 68 | 26.1 |

The examples show that, even with small amounts of stripping gas, it was possible to considerably lower the $O_2$ content in the liquid dinitrogen monoxide.

The losses of dinitrogen monoxide with the stripping gas are low and can be lowered even further by recycling the stripping gas into an earlier process stage.

Example 2

Process for Isolating and Purifying $N_2O$

The source used for the $N_2O$ is the offgas of a nitric acid plant, which is in turn operated with the offgas of an adipic acid plant and partially with pure NO. 26.2 t/h of this offgas are first compressed to 25 bar and cooled to 35° C. The water which condenses and also comprises small amounts of nitric acid is removed and disposed of.

The remaining compressed gas stream (26.1 t/h) comprises 86.4% by volume of $N_2$, 8.1% by volume of $N_2O$, 3.1% by volume of $O_2$ and 1.1% by volume of $CO_2$ as main components. This stream is fed in at the bottom of an absorption column of height 22.7 m and diameter of 5.5 m, which is filled with Pall rings. In countercurrent thereto, 2290 t/h of water are fed in from the top at a temperature of 35° C. The unabsorbed gas is decompressed through a decompression turbine back into the offgas line of the nitric acid plant.

The laden absorbent is decompressed to 1.1 bar by means of a decompression turbine in the first desorber tower. The desorber tower has a diameter of 3.6 m and height of 11.1 m and is filled with Pall rings. The water is conveyed back into the absorber tower. In this circuit, the pH is kept between 6 and 7 (measured online with calibrated glass electrodes) by adding 25% sodium hydroxide solution. An average of approx. 44 kg/h of sodium hydroxide solution are used.

In order to prevent the accumulation of salts (sodium nitrite, sodium nitrate and sodium hydrogencarbonate), 2 t/h are purged from the water circuit and replaced with fresh demineralized water. A heat exchanger in the water circuit is used to regulate the water temperature.

The gas (2.45 t/h) obtained at the top of the first desorber tower comprises 59.5% by volume of $N_2O$, 24.2% by volume of $N_2$, 7.5% by volume of $CO_2$, 5.2% by volume of $H_2O$ and 3.0% by volume of $O_2$ as main components. This gas is in turn compressed to 25 bar and cooled to 35° C. The water which condenses is removed and disposed of. The compressed gas stream is then introduced into a second absorber at the bottom together with the recycled gas streams from the partial condensation and the stripping. This absorber has a diameter of 1.9 m and a height of 14.3 m and is filled with Pall rings. In countercurrent thereto, water (274 t/a at a temperature of 35° C.) is introduced to the absorber as an absorbent.

The unabsorbed gas is decompressed and decompressed together with the offgas of the first absorber in the offgas line of the nitric acid plant.

The laden absorbent is then decompressed to 1.1 bar in the second desorber tower. The water is conveyed back into the absorber tower. In order to prevent the pH from falling, 225 kg/h are purged from the water circuit and replaced with fresh demineralized water. A heat exchanger in the water circuit is used to regulate the water temperature of the water.

The gas (2.9 t/h) obtained at the top of the second desorber tower comprises 81.7% by volume of $N_2O$, 10.7% by volume of $CO_2$, 5.3% by volume of $H_2O$, 1.7% by volume of $N_2$ and 0.45% by volume of $O_2$ as main components. This gas is in turn compressed to 26 bar and cooled to 13° C. The water which condenses is removed and disposed of.

The compressed gas stream (2.8 t/h) is then passed through an upright tube bundle heat exchanger which is operated on the jacket side with a cooled water/glycol mixture, where it is cooled to −12° C. This condenses a stream (2060 kg/h) which comprises 87.9% by volume of $N_2O$, 11.4% by volume of $CO_2$, 0.3% by volume of $H_2O$, 0.3% by volume of $N_2$ and 0.14% by volume of $O_2$ as main components.

In order to thaw the tubes of the heat exchanger, two parallel heat exchangers are used, which are operated in NB mode. In order to accelerate the thawing operation, the heat exchangers are provided with an electrical heater. The uncondensed fraction (790 kg/h) comprises 81.5% by volume of $N_2O$, 11.2% by volume of $CO_2$, 5.6% by volume of $N_2$ and 1.3% by volume of $O_2$ as main components and is recycled to the inlet of the second absorber as already mentioned above.

The condensed stream is then stripped in countercurrent with nitrogen (4 kg/h, corresponding to 19 mol of $N_2$/mol of $O_2$ in the liquid $N_2O$ feed) in a stripping column which is operated at 26 bar in trickle mode. The stripping column has a diameter of 0.35 m and a height of 4.15 m and is provided with a structured metal packing (packing length: 3 m) with a specific surface area of 350 $m^2/m^3$. The stripping gas at the top of the column (260 kg/h) comprises 78.4% by volume of $N_2O$, 10.8% by volume of $CO_2$, 9.6% by volume of $N_2$ and 1.0% by volume of $O_2$ as main components and is recycled to the inlet of the second absorber as already mentioned above.

The liquid product at the bottom of the stripping column (1835 kg/h) comprises 86.7% by volume of $N_2O$, 11.1% by volume of $CO_2$ and 1.9% by volume of $N_2$ as main components and only 100 ppm by volume of $O_2$.

The use of the stripping column allows the $O_2$ content in the liquid $N_2O$ to be reduced by a factor of 14. The molar $N_2O$ to $O_2$ ratio rises from 630 to almost 7300 mol/mol. As a result of the recycling of the stripping gas into the second absorption column, the isolated yield nevertheless remains high. The isolated yield of $N_2O$ (based on the compressed gas after the desorption) is 96.2%.

The concentrated and purified $N_2O$ can be used, for example, for the oxidation of olefins, for example of 1,5,9-cyclododecadiene.

Example 3

Influence of $O_2$ on the Decomposition of 1,5,9-cyclododecatriene

In order to study the influence of $O_2$ on the decomposition of 1,5,9-cyclododecatriene, 500 g of technical-grade 1,5,9-cyclododecatriene were initially charged in a 1000 ml glass flask equipped with a magnetic stirrer, a gas inlet tube and a reflux condenser. The flask was then heated to 180° C. in an oil bath, and 2 l (STP)/h of synthetic air were introduced through the gas inlet tube with a Brooks mass flow meter.

The offgas rate and composition thereof were determined at the outlet. In addition, samples of the liquid were taken and analyzed by gas chromatography at regular intervals. From the offgas analysis, an $O_2$ consumption of 11 mmol/h is calculated. The 1,5,9-cyclododecatriene content in the solution decreases at 2%/h. This means that 1.1 mol of 1,5,9-cyclododecatriene are destroyed per mole of $O_2$. Apart from small amounts of the monoepoxide of 1,5,9-cyclododecatriene, this does not form any defined products but merely polymeric deposits. A control test showed that, when only nitrogen instead of synthetic air is bubbled in, no decrease in the content of 1,5,9-cyclododecatriene is observed.

This test shows that, even at temperatures significantly below the temperature which is needed to oxidize 1,5,9-cyclododecatriene with $N_2O$ (approx. 250° C.), oxygen reacts with 1,5,9-cyclododecatriene. This forms polymeric deposits which can lead to blockage of the reactor. It is thus very important to use an $N_2O$-containing gas mixture which comprises a minimum amount of $O_2$ as an oxidizing agent, in order both to obtain a high selectivity and to prevent deposits in the reactor.

Example 4

Influence of $O_2$ on the Decomposition of 4,8-cyclododecadienone

In order to study the influence of $O_2$ on the decomposition of 4,8-cyclododecadienone (the product from the oxidation of 1,5,9-cyclododecatriene with $N_2O$), 500 g of 4,8-cyclododecadienone (approx. 98%, as an isomer mixture) were initially charged in a 1000 ml glass flask equipped with a magnetic stirrer, a gas inlet tube and a reflux condenser. The flask was then heated to 180° C. in an oil bath and 2 l (STP)/h of synthetic air were passed through the gas inlet tube with a mass flow meter.

The offgas rate and the composition thereof were determined at the outlet. In addition, samples of the liquid were taken and analyzed by gas chromatography at regular intervals. From the offgas analysis, an $O_2$ consumption of 8 mmol/h is calculated. The 4,8-cyclododecadienone content in the solution decreases at 1.6%/h. This means that 1.2 mol of 4,8-cyclododecadienone are destroyed per mole of $O_2$. This does not form any defined products, but no polymeric deposits either. A control test showed that when only nitrogen is bubbled in instead of synthetic air, no decrease in the 4,8-cyclododecadienone content is observed.

This test shows that, even at temperatures which are significantly below the temperature which is needed to oxidize 1,5,9-cyclododecatriene with $N_2O$ to 4,8-cyclododecadienone (approx. 250° C.), oxygen reacts with 4,8-cyclododecadienone (though, as expected, somewhat more slowly than with 1,5,9-cyclododecatriene). It is thus important to use an $N_2O$-containing gas mixture which comprises a minimum amount of $O_2$ as an oxidizing agent, in order to obtain a high selectivity.

Example 5

Oxidation of 1,5,9-cyclododecatriene with an $N_2O$-Containing Gas Mixture which Comprises only 200 ppm of $O_2$ For the continuous oxidation of 1,5,9-cyclododecatriene with $N_2O$, a jacketed tubular reactor which consists of 7 jacketed tube coils connected in series was used. The reaction tube has an internal diameter of 6 mm and each tube coil a length of 5.32 m. The total reaction volume was accordingly 1.05 liters. Within the jacket is circulated a heat carrier oil whose temperature is kept constant at 253° C. by means of a thermostat. The circulation rate of the heat carrier oil is selected such that the temperature difference between oil input and oil output is less than 2 K. The heat carrier oil is conducted in cocurrent to the reactants. The reactor is provided at the outlet with a pressure-regulating valve which keeps the reaction pressure constant at 100 bar.

The reactants (1,5,9-cyclododecatriene, commercial product from Degussa, and medical-grade $N_2O$ from Linde, comprises 200 ppm of $O_2$ according to analysis) are conveyed by means of suitable metering pumps (membrane piston pumps) and, upstream of the reactor, mixed in a static mixer at room temperature before they reach the reactor. The feed rates were adjusted such that the molar ratio between 1,5,9-cyclododecatriene and $N_2O$ at the reactor inlet is 6.2 mol/mol, and the residence time (defined as the volume flow of the reactants at room temperature and 100 bar divided by the reactor volume) is 0.65 hour. The reaction was carried out until the reactor was at a steady state (approx. 6 hours), before the mass balance was commenced. In order to minimize the errors, the mass balance time was always 24 hours.

Downstream of the pressure regulation valve, the reactor output was decompressed in a cooled (about 20° C.) phase separator, and the products (both gas and liquid) were analyzed. The 1,5,9-cyclododecatriene conversion was 13.4%. The selectivity for 4,8-cyclododecadienone based on 1,5,9-cyclododecatriene was 93.4%.

Example 6

Oxidation of 1,5,9-cyclododecatriene with an $N_2O$-Containing Gas Mixture which Comprises 400 ppm of $O_2$ and 8.3% by Volume of $CO_2$ Example 5 was repeated using, as the reactant, a gas mixture from Linde which comprised 8.3% by volume of $CO_2$ and 400 ppm of $O_2$ in $N_2O$.

The 1,5,9-cyclododecatriene conversion was 13.4%. The selectivity for 4,8-cyclododecadienone based on 1,5,9-cyclododecatriene was 93.8%.

Within the measurement accuracy, the presence of $CO_2$ and the slightly increased amount thus do not have any significant effect on the reaction.

Comparative Example 7

Oxidation of 1,5,9-cyclododecatriene with an $N_2O$-Containing Gas Mixture which Comprises 2% by Volume of $O_2$ Example 5 was repeated using, as the reactant, a mixture from Linde which comprised 2% by volume of $O_2$ in $N_2O$.

It was impossible to conduct the reaction stably with this feed. The pressure difference over the reactor rose continuously, and the test had to be stopped after 72 hours because the reactor was blocked. The first coil was then deinstalled and sawn into sections. It was found that the tube was almost completely blocked with polymeric deposits between 30 and 80 cm downstream of the reactor inlet.

With such high concentrations of $O_2$ in $N_2O$, stable operation of the 1,5,9-cyclododecatriene oxidation is impossible.

Comparative Example 8

Oxidation of 1,5,9-cyclododecatriene with an $N_2O$-Containing Gas Mixture which Comprises 1300 ppm by Volume of $O_2$ Example 5 was repeated using, as the reactant, a gas mixture from Linde which comprised 1300 ppm by volume of $O_2$ in $N_2O$.

The reaction was operable stably with this feed over 426 h. The pressure difference over the reactor remained constant. For inspection, the first coil was in turn deinstalled and sawn into sections. No polymer had deposited on the walls.

The 1,5,9-cyclododecatriene conversion at 14.6% was higher than in the inventive experiment (13.4%), though the selectivity for 4,8-cyclododecadienone was only 91.5%, i.e. almost 2% lower than in the inventive experiment (93.4%).

This experiment shows yet again the importance of minimizing the $O_2$ content in the $N_2O$ used.

The invention claimed is:

1. A process for purifying a gas mixture comprising dinitrogen monoxide, at least comprising the steps of:
   (I) at least partially condensing a gas mixture G-I comprising dinitrogen monoxide to obtain a liquid composition C-1 comprising dinitrogen monoxide, and
   (II) contacting the composition C-1 with a gas mixture M-1 to obtain a composition C-2 and a gas mixture M-2, wherein the gas mixture M-1 is selected from the group consisting of nitrogen, helium, neon, argon, krypton, xenon, hydrogen, carbon monoxide, methane, tetrafluoromethane, and mixtures thereof.

2. The process according to claim 1, wherein step (II) is performed continuously.

3. The process according to claim 1, wherein step (II) is performed in a bubble column.

4. The process according to claim 3, wherein the bubble column is operated in countercurrent.

5. The process according to claim 1, wherein the gas mixture G-I is obtained by a process comprising the steps of:
   (A) treating a gas mixture G-0 comprising dinitrogen monoxide to obtain a gas mixture G-A, at least comprising the steps of
      (i) absorbing the gas mixture G-0 in a solvent mixture S-I to obtain an offgas stream and a composition C-A and
      (ii) desorbing a gas mixture G-1 from the composition C-A to obtain a solvent mixture S-I'.

6. The process according to claim 5, wherein step (A) additionally comprises steps (iii) and (iv):
   (iii) absorbing the gas mixture G-1 in a solvent mixture S-II to obtain an offgas stream and a composition C-B
   (iv) desorbing a gas mixture G-2 from the composition C-B to obtain a solvent mixture S-II'.

7. The process according to claim 5, wherein the gas mixture M-2 is recycled into step (A).

8. The process according to claim 6, wherein the gas mixture M-2 is recycled into step (i) or into step (iii) of step (A).

* * * * *